US008815252B2

(12) United States Patent
Romanova et al.

(10) Patent No.: US 8,815,252 B2
(45) Date of Patent: Aug. 26, 2014

(54) METHOD FOR PRODUCTION OF PH STABLE ENVELOPED VIRUSES

(75) Inventors: Julia Romanova, Vienna (AT); Andrej Egorov, Vienna (AT); Brigitte Krenn, Vienna (AT); Markus Wolschek, Vienna (AT); Sabine Nakowitsch, Vienna (AT)

(73) Assignee: Baxter Healthcare SA, Glattpark (Opfikon) (CH)

( * ) Notice: Subject to any disclaimer, the term of this patent is extended or adjusted under 35 U.S.C. 154(b) by 191 days.

(21) Appl. No.: 13/129,806

(22) PCT Filed: Nov. 25, 2009

(86) PCT No.: PCT/EP2009/065812
§ 371 (c)(1),
(2), (4) Date: May 17, 2011

(87) PCT Pub. No.: WO2010/060921
PCT Pub. Date: Jun. 3, 2010

(65) Prior Publication Data
US 2011/0223199 A1    Sep. 15, 2011

Related U.S. Application Data

(60) Provisional application No. 61/117,900, filed on Nov. 25, 2008.

(30) Foreign Application Priority Data

Feb. 25, 2009   (EP) .................................... 09153664

(51) Int. Cl.
*A61K 39/145* (2006.01)
*C12N 7/00* (2006.01)
*C12N 7/08* (2006.01)

(52) U.S. Cl.
USPC ................... 424/209.1; 435/235.1; 435/237; 435/239; 424/205.1

(58) Field of Classification Search
None
See application file for complete search history.

(56) References Cited

U.S. PATENT DOCUMENTS

| 2007/0161085 A1 | 7/2007 | Trager |
| 2008/0014626 A1 | 1/2008 | Pohlscheidt |

FOREIGN PATENT DOCUMENTS

| EP | 1 911 836 A | 4/2008 |
| WO | WO 99/64068 | 12/1999 |
| WO | WO 99/64571 | 12/1999 |

OTHER PUBLICATIONS

Steinhauer et al., Proc Natl Acad Sci vol. 88, pp. 11525-11529, year 1991.*
Green et al., S Afr Med J Mar. 2008 vol. 98, No. 3, part 2, pp. 224-230-abstract only cited.*
International Search Report, International Application No. PCT/EP2009/065812, Apr. 6, 2010.
Maassab, H F, "Biologic and immunologic 1-14 characteristics of cold-adapted influenza virus," Journal of Immunology, vol. 102, No. 3, Mar. 1969, pp. 728-732.
Fiszman, M, et al., "Mode of action of acid 1-14 pH values on the development of vesicular stomatitis virus," Journal of Virology, vol. 13, No. 4, Apr. 1974, pp. 801-808.
Ackermann, W.W., et al., "Growth characteristics of influenza virus: the influence of a sulfonic acid," The Journal of Experimental Medicine, vol. 99, No. 2, Feb. 1954, pp. 105-117.
Alymova, et al., 1998, J Virol 72, pp. 4472-4477.
Mochalova, et al., 2003, Virology 313, pp. 473-480.
Romanova, et al., 2003, Virology 307, pp. 90-97.
Lin et al., 1997, Virology 233, pp. 402-410.
Ruigrok, et al., 1986, The EMBO Journal, vol. 5, No. 1, pp. 41-49.
Rachakonda, et al., 2007, Faseb J 21, pp. 995-1002.
Korte, et al., Eur Biophys J (2007) 36, pp. 327-335.
Shental-Bechor, et al., 2002, Biochim Biophys Acta 1565, pp. 81-89.
Steinhauer, et al., 1991, PNAS. 88, pp. 11525-11529.
Scholtissek, 1985, Archives Virol., 85, pp. 1-11.
International Written Opinion, International Application No. PCT/EP2009/065812, Apr. 6, 2010.
Bullough et al., "Structure of influenza haemagglutinin at the pH of membrane fusion," Nature, 371:37-43 (1994).
Genzel Y et al., Biotechnol. Prog., 21:58-69 (2005).
Mccahon D, Postgraduate Medical Journal, 49:195-199. (1973).
Skehel et al., "Receptor Binding and Membrane Fusion in Virus Entry: The Influenza Hemaglutinin," Annu. Rev. Biochem. 69:531-569 (2000).
Stegmann et al., "Effects of Low pH on Influenza Virus," Journal of Biological Chemistry, 262:17744-17749 (1987).
Suzuki T., Journal of Virology, 79(18):11705-11715 (2005).
Zhu Q, Journal of Virology, 82(1):220-228 (2008).

\* cited by examiner

*Primary Examiner* — Mary E Mosher
*Assistant Examiner* — Myron Hill
(74) *Attorney, Agent, or Firm* — Michael Fedrick; Loza & Loza, LLP

(57) ABSTRACT

The present invention provides a method for producing pH-stable enveloped viruses wherein said viruses are used for infection of host cells under low pH conditions and for incubation with cell culture cells under conditions of low pH, as well as influenza viruses obtainable by this method which exhibit a high growth rate in cell culture, increased pH and temperature stability and which have human receptor specificity.

4 Claims, 8 Drawing Sheets

Fig. 1 viral recovery after challenge

☐ BrisbaneΔNS
■ BrisbaneΔNS_HA2_N16I
▨ negative control

Fig. 2B attgacaaaatgaac → attgacattatgaac

METHOD FOR PRODUCTION OF PH STABLE ENVELOPED VIRUSES

CROSS-REFERENCE TO RELATED APPLICATIONS

This application is the U.S. national stage of International Patent Application No. PCT/EP2009/065812, filed on Nov. 25, 2009 and entitled "METHOD FOR PRODUCTION OF pH STABLE ENVELOPED VIRUSES", which claims the benefit of priority from European Patent Application No. 09153664.9, filed Feb. 25, 2009, and from U.S. Patent Application No. 61/117,900, filed Nov. 25, 2008. The disclosures of the foregoing applications are incorporated herein by reference in their entirety.

SEQUENCE LISTING

The entire content of a Sequence Listing titled "Sequence_Listing.txt," created on May 16, 2011 and having a size of 1 kilobyte, which has been submitted in electronic form in connection with the present application, is hereby incorporated by reference herein in its entirety.

FIELD OF THE INVENTION

The present invention provides a method for producing pH-stable enveloped viruses wherein said viruses are incubated with cell culture cells under conditions of low pH. Such viruses include novel influenza viruses which show high growth rate in cell culture, increased pH and temperature stability and which have human receptor specificity.

BACKGROUND

For preventing disease caused by annual epidemics of viral infections, vaccination is the most important public health measure. An effective supply of vaccines is dependent on being able to quickly produce large quantities of vaccine material (e.g. virus). The rapid development of vaccines and their abundant availability is critical in combating many human and animal diseases. Delays in producing vaccines and shortfalls in their quantity can cause problems in addressing outbreaks of disease.

Growth of viruses, especially of influenza virus in embryonated chicken eggs, has been shown to result in effective production of influenza virus particles which can be either used for production of inactivated or live attenuated influenza virus vaccine strains. Nevertheless during the last few years intensive efforts have been made in establishing virus production systems using cell culture because an egg-based method requires a steady supply of specific pathogen-free eggs which could be problematic in case of a pandemic. The cell-based technology is an alternative production process that is independent of eggs suppliers and can be started as soon as the seed virus is available. Besides this, inactivated influenza vaccine prepared from the virus grown in mammalian cells was shown to induce more cross-reactive serum antibodies and reveals better protection than egg-grown vaccine (Alymova et al., 1998, *J Virol* 72, 4472-7). Moreover, according to previous results receptor specificity and antigenic properties of human isolates become altered following growth of the virus in embryonated chicken eggs (Mochalova et al., 2003, *Virology* 313, 473-80, Romanova et al., 2003, *Virology* 307, 90-7).

On the other hand, multiple propagation of viruses in tissue culture often results in HA mutants that have elevated pH of fusion (Lin et al., 1997, *Virology* 233, 402-10) which is correlated to decreased stability to thermal denaturation of viruses (Ruigrok et al., 1986). The structure of any protein and its stability are based on noncovalent interactions like hydrophobic forces, van der Waal interactions, hydrogen bonds, and ionic interactions. Mutations which appear upon adaptation of viruses to cell cultures are known to elevate the threshold of pH of fusion induced by reduced protein stability because of changed ionic interactions and salt bridges in HA molecule (Rachakonda et al., 2007, *Faseb J*21, 995-1002). Destabilizing mutations usually found either at the interface HA1-HA2 or HA2-HA2 regions or in the N terminus of HA2 in turn could lead to reduced binding to cell-surface receptors (Korte et al., 2007, Rachakonda et al., 2007, *Faseb J* 21, 995-1002, Shental-Bechor et al., 2002, *Biochim Biophys Acta* 1565, 81-9), which leads to decreased virus infectivity and subsequently reduced immunogenicity of live virus preparations.

Massaab (Massaab H. F., Journal of Immunology. 1969, 102, pp. 728-732) tested the biologic and immunologic characteristics of cold-adapted influenza virus using different genetic markers before and after adaptation to growth in primary chick kidney tissue culture and embryonated eggs. It is stated that these strains are more sensitive to low pH compared to original "wild type" strains and showed marked decrease in infectivity and hemagglutination yields.

Fiszman et al (Journal of Virology, 1974, 13, pp. 801-808) examined the effect of low pH (pH6.6) on vesicular stomatitis virus (VSV) and showed that no viral particles or nucleocapsids were detected. Ackermann W and Massaab H. F. (Journal of Experimental Medicine FEB 1954, 99, pp 105-117) disclosed the effect of a viral inhibitor, alpha-amino-p-methoxy-phenylmethanesulfonic acid) upon the growth cycle of influenza virus.

Due to difficulties in obtaining high amounts of vaccine virus preparations from cell culture which are of high stability and immunogenicity in order to avoid any safety or supply issues, it is an object of the present invention to make available processes which lead to efficacious and stable viruses. The object is achieved by the provision of the embodiments of the present application.

The invention relates to a method for producing pH stable enveloped viruses in tissue cultures by employing conditions of decreased pH during dilution of virus suspension and host cell infection. The method of the invention also provides virus of increased stability and immunogenicity compared to virus particles derived from presently used methods.

FIGURES

Figure 1:
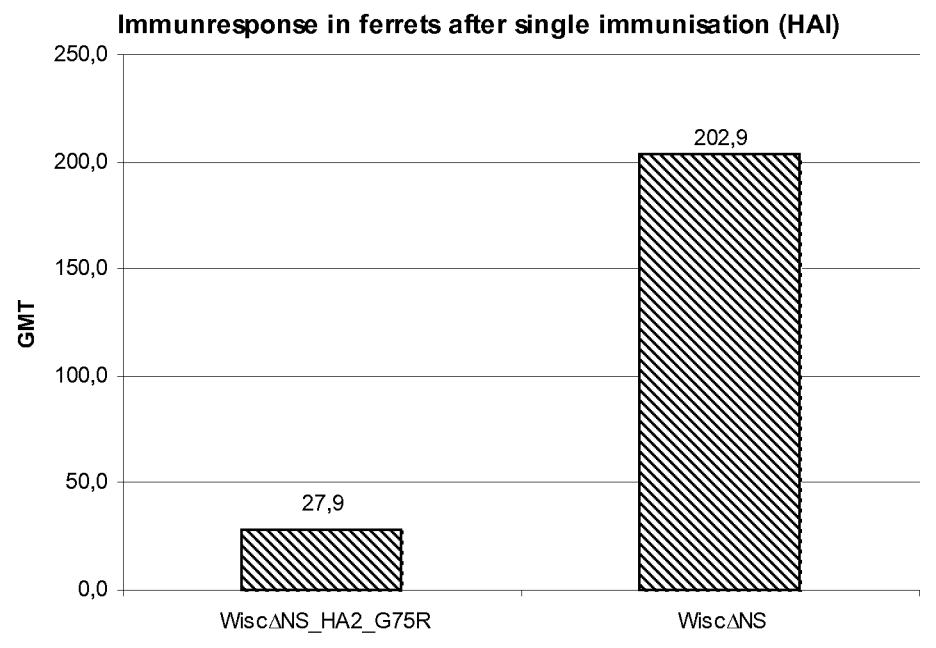

FIG. 1: Immunogenicity of Wisc.ΔNS1 and Wisc.ΔNS1_HA2_G75R compared in ferrets after single intranasal immunization with the dose of 6.0 log TCID50/animal.

FIG. 2
A) Induction of serum antibodies in mouse model.
B) Reproduction of challenge virus in the lungs and nasal turbinates of immunized mice.

FIG. 3
A. Sequence comparison of HA molecule of original and mutant viruses (SEQ ID No. 1 and SEQ ID No. 2, respectively). Substitutions of two nucleotides (aa) to (tt) by site directed mutagenesis led to the amino acid change K to I at position 58 of HA2 subunit.
B. Fusion activity of VN1203 and VN1203 K58I viruses with human erythrocytes.

C. IgA antibody titers in mouse nasal washes after immunization with VN1203 and VN1203 K58I viruses.
D. HAI antibody titers in mouse sera after immunization with VN1203 and VN1203 K58I viruses.
E. Infectivity of VN 1203 and VN1203K58I viruses for mice.

FIG. 4: Sensitivity of Vienna/28 and Vienna/28_HA2_G75R viruses towards low pH.

DETAILED DESCRIPTION OF THE INVENTION

The invention relates to a method for producing enveloped viruses characterized in that it comprises following steps:
a) diluting viruses in a solution having a pH between 5.2 and 5.9, preferably between 5.4 and 5.8, most preferably at about 5.6;
b) infecting host cells with at least one infectious virus particle wherein i) the virus particle is added to said cells and ii) said cells and said virus particle are incubated at a pH between 5.2 to 5.9, preferably between 5.4 and 5.8, most preferably at about 5.6 to provide a virus/cell complex;
c) cultivating the infected host cells to propagate viruses;
d) harvesting the viruses and optionally;
e) purifying and/or characterising the viruses.

The virus obtained by said method can be used for production of lab scale amounts of virus as well as for large scale production of vaccine virus.

"Large scale production" means the production in a minimum cultivation volume of at least 200l, preferably of at least 500l, preferably of about 1000l:

Vaccine preparations containing enveloped viruses have to be immunogenic to provide sufficient vaccination. Especially, inactivated pandemic influenza vaccines like against avian influenza can be poorly immunogenic and require high doses to elicit protective antibody responses in humans. Effective antibody responses provide crucial immunity against virus infection. The hemagglutinin (HA) protein is the major target of protective antibody responses induced by viral infection with influenza virus and by vaccination with both inactivated and live-attenuated flu vaccines. The structure integrity of HA antigens is critical for eliciting protective antibody responses.

The inventors have shown that the inventive method provides viruses that comprise pH stability and increased immunogenicity. The HA protein of the virus particles so produced preferably shows increased stability at low pH. Advantageously the viruses can also show increased stability at higher temperatures, specifically at temperatures up to 60° C. These viruses do not significantly lose hemagglutination activity of HA even when stored at increased temperatures like e.g. at 60° C. for several minutes up to several hours. "Not significant" means that hemagglutination activity is decreased less than fourfold compared to the source virus. Even after exposure to increased temperatures, said viruses keep stability when stored for several weeks up to several months at a temperature between 0° C. and 12° C., preferably at 4° C. Therefore the viruses produced according to the invention are highly advantageous for vaccine preparation as said viruses comprise a stable HA molecule.

This method can be used specifically for negative-strand RNA viruses which are a group of animal viruses that comprise several important human pathogens, including influenza, measles, mumps, rabies, respiratory syncytial, Ebola and hanta viruses.

The genomes of these RNA viruses can be unimolecular or segmented, single stranded of (−) polarity. Two essential requirements are shared between these viruses: the genomic RNAs must be efficiently copied into viral RNA, a form which can be used for incorporation into progeny virus particles and transcribed into mRNA which is translated into viral proteins. Eukaryotic host cells typically do not contain machinery for replicating RNA templates or for translating polypeptides from a negative stranded RNA template. Therefore negative strand RNA viruses encode and carry an RNA-dependent RNA polymerase to catalyze synthesis of new genomic RNA for assembly into progeny and mRNAs for translation into viral proteins.

Genomic viral RNA must be packaged into viral particles in order for the virus to be transmitted. The process by which progeny viral particles are assembled and the protein/protein interactions occur during assembly is similar within the RNA viruses. The formation of virus particles ensures the efficient transmission of the RNA genome from one host cell to another within a single host or among different host organisms.

Virus families containing enveloped single-stranded RNA of the negative-sense genome are classified into groups having non-segmented genomes (Paramyxoviridae, Rhabdoviridae, Filoviridae and Borna Disease Virus, Togaviridae) or those having segmented genomes (Orthomyxoviridae, Bunyaviridae and Arenaviridae). The Orthomyxoviridae family includes the viruses of influenza, types A, B and C viruses, as well as Thogoto and Dhori viruses and infectious salmon anemia virus.

Preferred embodiments include but are not limited to influenza virus, respiratory syncytial virus (RSV), Newcastle disease virus (NDV), vesicular stomatitis virus (VSV), and parainfluenza virus (PIV).

Influenza virions consist of an internal ribonucleoprotein core (a helical nucleocapsid) containing the single-stranded RNA genome, and an outer lipoprotein envelope lined inside by a matrix protein (M1). The segmented genome of influenza A virus consists of eight molecules of linear, negative polarity, single-stranded RNAs which encodes eleven (some influenza A strains ten) polypeptides, including: the RNA-dependent RNA polymerase proteins (PB2, PB1 and PA) and nucleoprotein (NP) which forms the nucleocapsid; the matrix membrane proteins (M1, M2); two surface glycoproteins which project from the lipid containing envelope: hemagglutinin (HA) and neuraminidase (NA); the nonstructural protein (NS1) and nuclear export protein (NEP). Most influenza A strains also encode an eleventh protein (PB1-F2) believed to have proapoptotic properties.

Transcription and replication of the genome takes place in the nucleus and assembly occurs via budding on the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed by a unique mechanism in which viral endonuclease cleaves the capped 5'-terminus from cellular heterologous mRNAs which then serve as primers for transcription of viral RNA templates by the viral transcriptase. Transcripts terminate at sites 15 to 22 bases from the ends of their templates, where oligo(U) sequences act as signals for the addition of poly(A) tracts. Of the eight viral RNA molecules so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NEP. In other words, the eight viral RNA segments code for eleven proteins: nine structural and two nonstructural (NS1 and the recently identified PB1-F2) proteins.

The viruses may be selected from naturally occurring strains, variants or mutants; mutagenized viruses (e.g. generated by exposure to mutagens, repeated passages and/or passage in non-permissive hosts); reassortants (in the case of segmented viral genomes); and/or genetically engineered viruses (e.g. using the "reverse genetics" techniques) having the desired phenotype.

The term "passaged" is defined as inoculating host cells with a defined virus particle number and harvesting said virus after a defined number of days, typically 2-3 days. The viruses will have approx. 2 to 4 replication rounds per day.

It is well known in the art that the wild-type viruses used in preparation of the vaccine strains for annual vaccination against epidemic influenza are recommended annually by the World Health Organization (WHO). These strains may then be used for the production of reassortant vaccine strains which generally combine the NA and/or HA genes of the wild-type viruses with the remaining gene segments derived from a donor virus (often referred to as a master donor virus or MDV) which will have certain desirable characteristics. For example, an MDV strain may be cold-adapted temperature sensitive, attenuated, and/or has a high growth rate.

According to a specific embodiment, the influenza virus is an attenuated influenza virus. Specifically the influenza virus comprises deletions or modifications within the pathogenicity factors inhibiting innate immune response of host cells. The attenuation can exemplarily be derived from cold-adapted virus strains or due to a deletion or modification within the NS1 gene (ΔNS1 virus) as described in WO99/64571 and WO99/64068 which are incorporated herein in total by reference. These viruses are replication deficient as they undergo abortive replication in the respiratory tract of animals. Alternatively, the viruses can comprise deletion or modification of the PB1-F2 gene.

According to the invention the virus can further comprise modifications within the HA gene which can increase the stability of the HA molecule. For example, Steinhauer et al. (1991, PNAS. 88: 11525-1152) identified the K58I mutation in the $HA_2$ of influenza Rostock virus (H7N1) to be responsible for a decreased pH value of membrane fusion compared to the non-mutated virus. This implies that the conformational change of the HA induced by the acidic pH happens in the mutated form of the HA at 0.7 lower pH compared to the wildtype virus. By introducing this mutation to the X-31 influenza virus (H3 subtype) the same effect was shown.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

Specifically, the influenza virus vaccines are derived from interpandemic or pandemic influenza virus strains, for example of H1, H3 or B strains. It has been shown that these strains show highly increased immunogenicity when produced according to the inventive method.

The cells which can be used in the method according to the invention for cultivating the viruses can be any desired type of cells which can be cultured and which can be infected by enveloped viruses, specifically by influenza viruses. Specifically it can be BSC-1 cells, LLC-MK cells, CV-1 cells, CHO cells, COS cells, murine cells, human cells, HeLa cells, 293 cells, VERO cells, MDBK cells, MDCK cells, CEK (chicken embryo kidney) CEF (chicken embryo fibroblasts), MDOK cells, CRFK cells, RAF cells, TCMK cells, LLC-PK cells, PK15 cells, WI-38 cells, MRC-5 cells, T-FLY cells, BHK cells, SP2/0 cells, NS0, PerC6 (human retina cells).

For diluting the viruses any buffer can be used which can provide the range of pH values, specifically between pH 5.2 and 5.9, specifically between 5.4 and 5.8 and which is physiological for the cells. For example, it can be MES (2-(N-morpholino-ethanesulfonic acid) buffer, citric buffer or acetic buffer, specifically using buffers based on PBS. Additionally components can also be added to the dilution solution, for example salts like sodium chloride, di-sodium hydroxy-phosphate or potassium di-hydroxy-phosphate etc.

The term dilution means that virus suspension is diluted to a content of virus particles that is sufficient for productive infection of cells.

According to the inventive method appropriate cells are infected with at least one virus particle. The number of virus particles necessary for sufficient infection can be easily determined by the skilled person. The infection of the cells with the viruses can be specifically carried out at an m.o.i. (multiplicity of infection) of about 0.0001 to 10, preferably of 0.001 to 0.5.

Optionally, a macrolide polyene antibiotic or a derivative can be present during the dilution step in the dilution solution and/or during infection and/or cultivation. Specifically, the antibiotic is amphotericin B or a derivative thereof. Specifically, the macrolide polyene antibiotic can be added before infection, for example about 60-30 minutes before, more preferably 30 minutes before infection. Optimal concentration of antibiotic used for virus incubation or cultivation is between 0.20 and 0.50 µg/ml, specifically 0.25 µg/ml.

The temperature for incubating the virus for binding it to the cells, especially to the cellular receptors, can be between 20° C. and 38° C. The pH for incubation is preferably between 5.4 and 5.8. For determination of the time sufficient for internalization of the virus into the cell, virus can be monitored by standard procedures, like labelling with a dye or electron microscopy. Specifically, the time period is between at least 5 minutes and 60 minutes, preferably between 20 and 60 minutes at room temperature.

A protease which cleaves the precursor protein of hemagglutinin can be added and the internalization of the viruses to the cells can be carried out according to the invention shortly before, simultaneously with or shortly after the infection of the cells with influenza viruses. If the addition is carried out simultaneously with the infection, the protease can either be added directly to the cell culture to be infected or, for example, as a concentrate together with the virus inoculate. The protease is preferably a serine protease, and particularly preferably trypsin. If trypsin is used, the final concentration added in the culture medium is advantageously 1 to 200 µg/ml, preferably 5 to 50 µg/ml, more preferably 5 to 30 µg/ml.

After infection, the infected cell culture is cultured further to replicate the viruses, in particular until a maximum cytopathic effect or a maximum amount of virus antigen can be detected. The harvesting can alternatively be at any time point during cultivation.

The pH for cultivation of the host cells, can be for example between 6.5 and 7.5. The pH for cultivation depends on the pH stability of the host cells used for cultivation. This can be determined by testing of the host cells' viability under different pH conditions.

The terms cultivation and propagation do have the same meaning according to the invention.

For cultivation any medium useable for cultivation of cells is appropriate. Specifically the medium can be SFM Optipro™ medium, a low protein medium for the culture of kidney epithelial and related cells expressing virus. Cells can be cultivated at a temperature between 20 and 40° C., specifically between 30 and 40° C.

The viruses can be passaged in the host cells for at least one passage, yet usually several passages are needed, for example at least three passages.

According to a specific embodiment of the method, the harvesting and isolation of the replicated influenza viruses is carried out 2 to 10 days, preferably 3 to 7 days, after infection. The cells or cell residues can be separated and harvested from the culture medium by means of methods known to the person skilled in the art, for example by separators or filters. Following this concentrating, the influenza viruses present in the cultivation medium is carried out by methods known to the person skilled in the art, such as, for example, gradient centrifugation, filtration, precipitation and the like.

It was shown successfully by the inventors that diluting enveloped viruses and infecting cells under low pH conditions lead to enveloped viruses which show stability at low pH and increased immunogenicity. These viruses can also show stability at increased temperatures and/or high growth rates in cell culture and/or human receptor specificity. This is surprising as Scholtissek (1985, Archives Virol., 85, 1-11) showed at low pH values infectivity of influenza viruses was irreversibly lost. It was also stated that there is no correlation between the pH and heat stability.

As a further embodiment of the invention, an influenza virus is also provided that is for example useful as seed virus or virus useful for vaccination purposes. Said influenza virus retains detectable hemagglutination activity at increased temperature, retains infectivity stable at pH range of 5.4 and 5.8, is of high growth rate in cell culture and has human receptor specificity.

"Seed virus" is defined as the virus used to inoculate a cell culture.

Detectable hemagglutination activity according to the embodiment of the invention is defined as a not more than fourfold decrease of hemagglutination activity compared to the source virus as used. The source virus can be for example virus directly isolated from a nasal swab.

According to a further embodiment virus can be provided that is useful as vaccine virus. Said virus particles are stable at low pH and show immunogenicity which is similar or increased compared to virus obtained by known cell culture procedures, for example from Vero cells, MDCK or MDBK cells. Specifically the virus shows increased growth rate in cell culture compared to virus that has not been exposed to the method according to the present invention. Further, the virus is temperature stable and has human receptor specificity.

Temperature stability according to the present invention means that hemagglutination activity is not significantly decreased at a temperature of up to 60° for a time period of up to 15 minutes. pH stability is defined as stability of the virus at a pH of 5.6, preferably between 5.4 and 5.8, preferably between 5.2 to 5.9. High growth rate means a growth rate of up to 6 log TCID 50/ml, preferably above 7 log TCID 50/ml.

Said virus can be obtained by the method as described in the present application. The viruses are particularly useful for vaccine formulations or therapeutic formulations. Influenza virus contained in these formulation can be either attenuated virus or inactivated virus. Inactivation can be performed by any method as known in the art, like treatment with formalin or other agents used in the manufacturing of killed virus vaccines or treatment with non-ionic detergents or exposure to UV light. Influenza virus comprising preparations can be administered by any route like for example subcutaneously, intranasally or intramuscularly.

Alternatively, the preparations containing the influenza virus can further comprise pharmaceutically acceptable carriers or adjuvants known to enhance immunogenicity of the administered preparation.

Preferably, the preparations are administered via the mucosa, specifically by intranasal application as these viruses are of high immunogenicity being a result of the above listed characteristics, i.e. pH stability, temperature stability, high growth rate and human receptor specificity.

An influenza virus comprising these characteristics has never been described or indicated before.

The foregoing description will be more fully understood with reference to the following examples. Such examples are, however, merely representative of methods of practicing one or more embodiments of the present invention and should not be read as limiting the scope of invention.

EXAMPLES

Example 1

Two influenza strains bearing surface glycoproteins from epidemic strain A/Wisconsin/67/05 (H3N2) and all other genes from WHO vaccine strain IVR-116 (reassortant of A/New Caledonia/20/99 and A/Puerto Rico/8/34) in combination with NS gene lacking the NS1 open reading frame (ΔNS1) were constructed by reverse genetics. Obtained viruses differed by one amino acid substitution in the sequence of HA molecule, due to different passaging conditions on Vero cells. First virus, named Wisc.ΔNS1 was always passaged on Vero cells with pre treatment of virus inoculum with low pH buffer, namely:
the virus was diluted in a MES infection buffer (0.1 M MES, 150 mM NaCl, 0.9 mM $CaCl_2$, 0.5 mM $MgCl_2$; pH=5.6) supplemented with 0.25 µg/ml amphotericin B to appropriate moi. Vero cells were washed with infection buffer and the virus inoculum was applied to the cells and incubated for 30 min. Then the inoculum was removed and cells were incubated in serum free Opti-pro medium supplemented with 0.25 µg/ml amphotericin B and 5 µg/ml trypsin.

This method resulted in the preservation of the original virus HA sequence found in the clinical swab. Second virus was propagated by standard way at neutral conditions and acquired one substitution in HA2 subunit, namely G75R (Table.1). Table 1 shows the sequence comparison of HA molecule comparing to virus present in the swab.

The HA nucleotide sequences of two viruses cultivated at different conditions were compared. Virus Wisc.ΔNS did not acquire any mutations in HA molecule, while one mutation G75R located in HA2 subunit was identified in the virus Wisc.ΔNS_HA2_G75R.

TABLE 1

|  | Substitutions in HA subunits | |
| --- | --- | --- |
| Viruses | HA1 | HA2 |
| Wisc.ΔNS | none | None |
| Wisc.ΔNS_HA2_G75R | none | G75R |

Next both viruses were compared in their stability toward low pH by the next method. The virus was diluted in the infection MES buffer having the pH range 5.6-7.5 in order to get a defined moi and applied to the Vero cells with subsequent incubation for 30 min to allow the virus to infect cells. Afterwards the inoculum was removed, cells were incubated at 37° C. for 4-9 h (depending on the strain) then fixed and influenza NP protein was detected by immunofluorescence.

This test revealed that virus Wisc.ΔNS1 appeared to be stable at pH 5.6 infecting the cells with the same efficiency as at neutral conditions, while mutant virus Wisc.ΔNS1_HA2_G75R completely lost the ability to infect cells at pH 5.6 infecting cells only at pH 5.8 with the same efficiency as at neutral conditions (results are not shown).

The immunogenicity of Wisc.ΔNS1 and Wisc.ΔNS1_HA2_G75R viruses was compared in ferrets after single intranasal immunization with the dose of 6.0 log TCID50/animal. The obtained results demonstrated that virus with intact sequence of HA Wisc.ΔNS1 induced significantly higher serum antibody titers, measured by HAI test (GMT 202.9), than the virus Wisc.ΔNS1_HA2_G75R (GMT 27.9) (FIG. 1).

Example 2

Two H1N1 influenza strains bearing surface glycoproteins from epidemic strain A/Brisbane/59/07 (H1N1) and all other genes from WHO strain IVR-116 in combination with NS gene lacking the NS1 open reading frame (ΔNS1) were constructed by reverse genetics. Obtained viruses differed by one amino acid substitution in the sequence of HA molecule, appeared due to different passaging conditions on Vero cells. First virus, named BrisbaneΔNS1 was passaged at low pH conditions in the presence of amphotericin B. This procedure resulted in the preservation of the HA sequence, which appeared to be similar to that of virus isolated in MDCK cells from clinical sample (passage 1).

Second virus, named BrisbaneΔNS1_HA2_N16I was passaged by standard method and acquired one substitution in HA2 subunit, namely N16I (Table 2). Tab. 2 shows the sequence comparison of HA molecule comparing to initial isolate.

TABLE 2

| Viruses | Substitutions in HA subunits | |
|---|---|---|
| | HA1 | HA2 |
| BrisbaneΔNS | none | none |
| BrisbaneΔNS_HA2_N16I | none | N16I |

The HA nucleotide sequences of two viruses cultivated at different conditions was compared. Virus BrisbaneΔNS did not acquire any mutations in HA molecule, while one mutation N16I located in HA2 subunit was identified in the virus BrisbaneΔNS_HA2_N16I.

Comparison of virus stability towards low pH revealed that virus BrisbaneΔNS1 appeared to be stable. In immune fluorescent assay the same amount of stained Vero cells at pH as low as 5.6 and pH 7.5 was observed. Mutant virus BrisbaneΔNS1_HA2_N16I was less stable infecting cells only at pH 5.8 and did not infect any at pH 5.6. No immune fluorescent signal was visible on the cells infected with the virus combined with buffer pH 5.6 (results are not shown).

Immunogenicity of both viruses was compared after single intranasal immunization of mice with virus dose 5.6 log TCID50/animal. The obtained results revealed that virus BrisbaneΔNS1 was more immunogenic than BrisbaneΔNS1_HA2_N16I inducing higher levels of serum antibodies (measured by HAI test) and better protection of animals indicated by reduced replication of the challenge virus in the lungs and nasal turbinates of mice (FIG. 2A, B). FIG. 2B specifically discloses the reproduction of challenge virus in the lungs and nasal turbinates of immunized mice.

Example 3

Cultivation of influenza B strains on Vero cells at standard conditions also leads to the appearance of destabilizing mutations either at the interface HA1-HA2 or HA2-HA2 regions in HA molecule related to the decreased stability and in turn decreased immunogenicity of mutated virus in animal models (data not shown).

Example 4

Previously it was found that H5N1 avian highly pathogenic viruses circulated during last decade do not stand treatment with human nasal washings, having a pH of 5.6. They also did not stand treatment with acidic buffer with the same pH 5.6 during inoculation of Vero cells. It was found that the reason of this instability is high pH at which HA molecule changes the conformation in order to perform fusion with the cell membrane, which for H5N1 virus has the value pH 5.6 while for human viruses it is in the range of 5.2-5.4.

Steinhauer et al., have demonstrated that one substitution in HA2, namely K58I of H7N7 virus could decrease significantly the pH of fusion by 0.7 units. Introduction of this mutation in H3N2 virus had a similar effect.

This change was introduced by site-directed mutagenesis to the HA protein of the A/VN1203/04 ΔNS1 (H5N1) virus (reassortant, inheriting the HA, NA, and M genes from A/VN/1203/04 and the remaining genes from the IVR-116 vaccine strain in combination with ΔNS1 gene) and named the rescued virus VN1203 HA K58I (FIG. 3A). FIG. 3A shows the sequence comparison of HA molecule of original and mutant viruses)

HA of both viruses was modified in a trypsin dependent manner. The pH of fusion for mutated virus VN1203 HA K58I was reduced on 0.3 units in hemolisis experiment with human erythrocytes (data not shown).

Moreover, virus VN1203 HA K58I showed reduced loss of infectivity at pH 5.6. In immune fluorescent assay it was observed almost similar amount of stained cells after infection made at pH 5.6 and 7.5 with virus VN1203 HA K58I, while no stained cells were visible when infection was done with VN1203 virus at pH 5.6 (data not shown).

The ability of both viruses was compared to induce the immune response after intranasal immunization of mice. After 4 weeks post immunization mouse sera and nasal washings were obtained and HAI and IgA antibodies were measured. As presented on FIG. 3B, VN1203 HA K58I virus induced 4 times higher titers of IgA antibodies than virus VN1203 with original HA sequence.

In order to prove that increased HA stability towards low pH leads to better virus infectivity for mammals, two analogous reassortants VN1203R and VN1203R HA K58I comprising competent NS gene were constructed. Presence of competent NS gene was necessary for the efficient viral growth in respiratory tract of immuno-competent organisms. The viral growth of both viruses in the upper respiratory tract after intranasal inoculation with each of these viruses taken in different doses was compared. It was found that virus having mutated HA VN1203R HA K58I was 100 times more infectious for mice growing in the upper respiratory tract at $MID_{50}$ (mouse infectious dose—dose infecting 50% of mice) value 2.5 log in comparison to 4.5 log $MID_{50}$ of non-modified VN1203R virus (FIG. 3E).

Figure 2A:
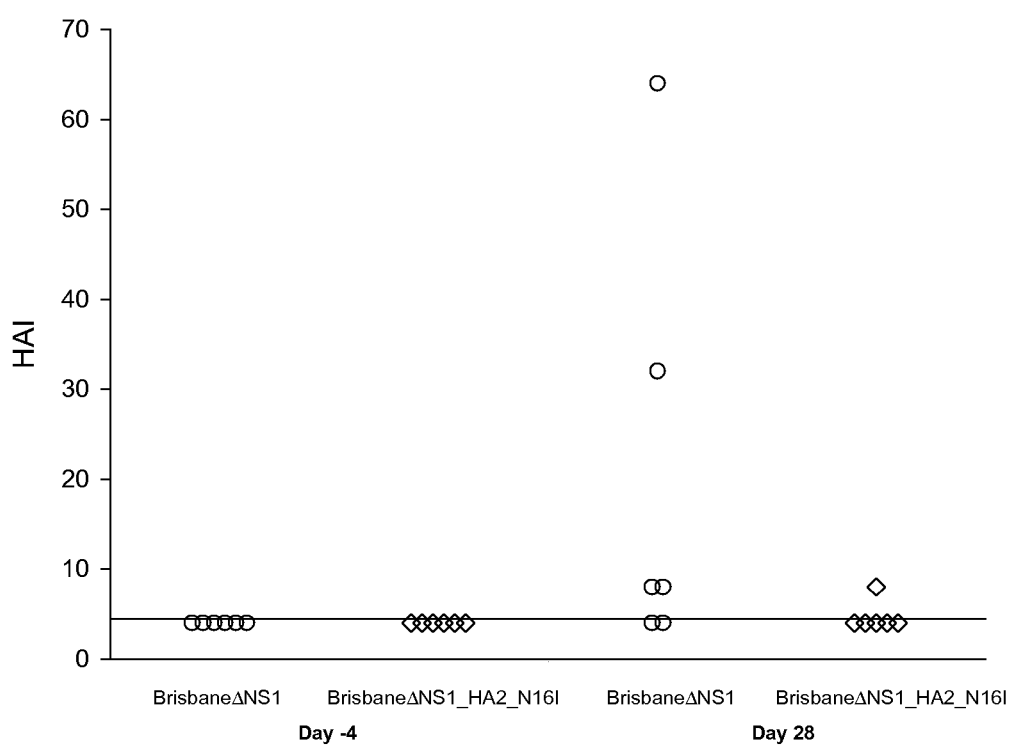
Figure 3C:
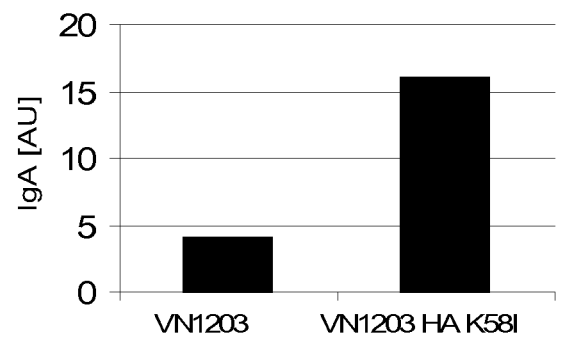
Figure 3D:
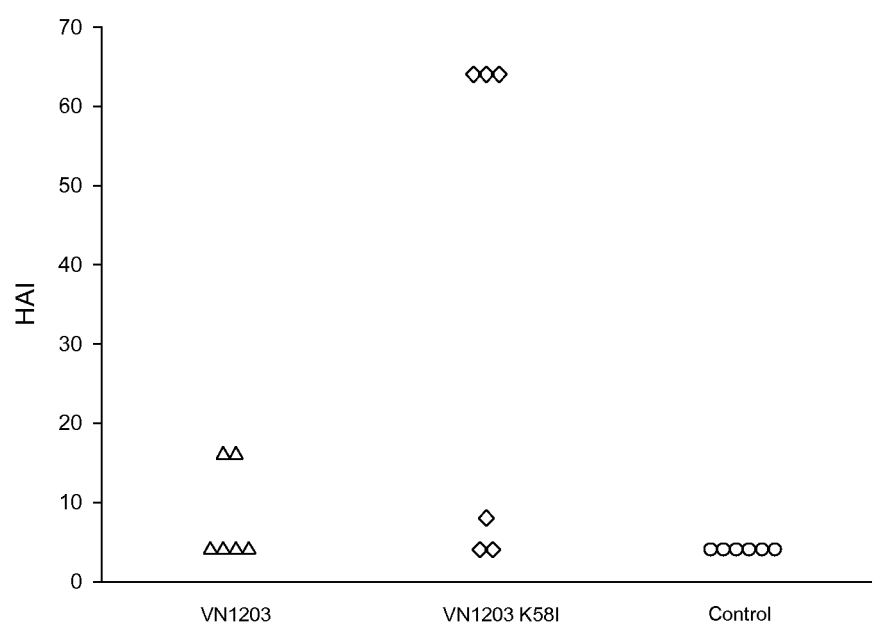
FIG. 3B shows the IgA antibody titers in mouse nasal washes after immunization with VN1203 and VN1203 K58I viruses.
FIG. 3C shows HAI antibody titers in mouse sera after immunization with VN1203 and VN1203 K58I viruses.
Figure 3E:
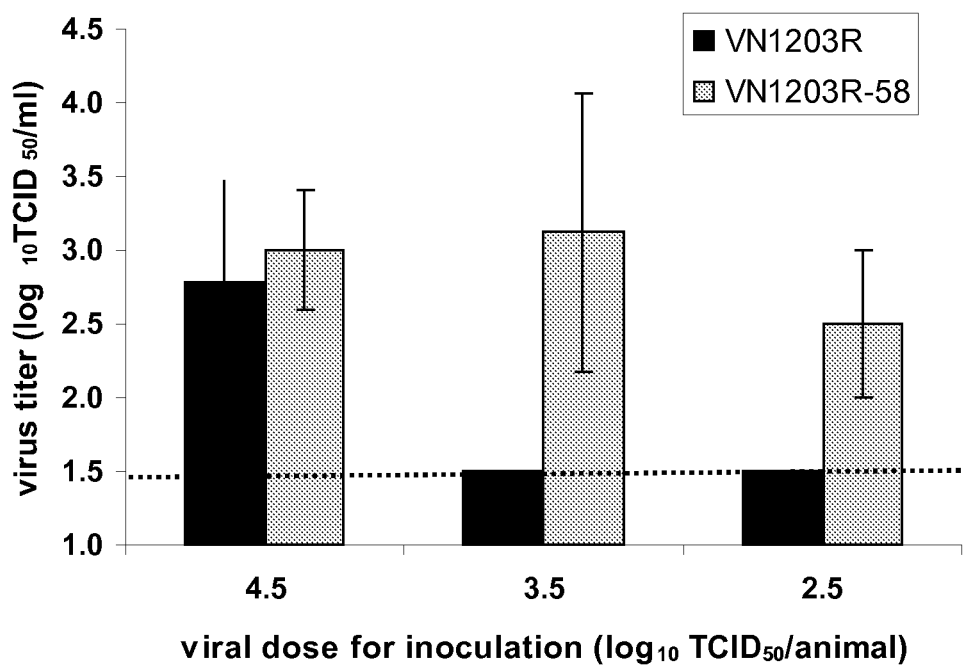

FIG. 3E shows the reproduction of viruses in the upper respiratory tract of mice after intranasal infection with different doses

Example 5

Thermostability

Propagation of viruses with acidic inoculation preserved also virus stability to thermo inactivation. Thermo stability was checked by titration of virus hemagglutination titer after incubation of viruses at elevated temperatures for 15 min. It was found that viruses which were cultivated with low pH inoculation (BrisbaneΔNS1 H1N1, WisconsinΔNS1 H3N2, BrisbaneΔNS1 H3N2) retained hemagglutination activity even after exposure to 60° C. Viruses cultivated at standard conditions and acquired destabilizing mutations in HA (New Caledonia ΔNS1_HA2_113, WisconsinΔNS1_HA_218_225_75_81 H3N2) were not able to stand treatment at 60° C. and completely lost hemagglutination activity after 15 min (Table 1).

As regards to avian influenza viruses, it was found that strains containing HA with the only modification of polybasic cleavage site (in a trypsin dependent manner) did not stand even treatment at 55° C. (HongKong156ΔNS1 H5N1, VN1203(6:2) (H5N1), VN1203 H5N1) loosing completely the ability to agglutinate erythrocytes in 15 min of treatment. The threshold for these viruses was 50° C. Introduction of mutation K58I in HA2 subunit of HA ectodomain increased virus stability until 55° C.

reassortants inheriting HA, NA and M (in case of 5:3) genes of avian viruses A/Vietnam/1203/04 or A/Hong Kong/156/97 and all other genes from IVR-116 strain. HA cleavage site of highly pathogenic avian strains was substituted to that of low pathogenic avian viruses. All avian viruses in this study contained NS gene lacking the NS1 open reading frame.

Example 6

Figure 4:
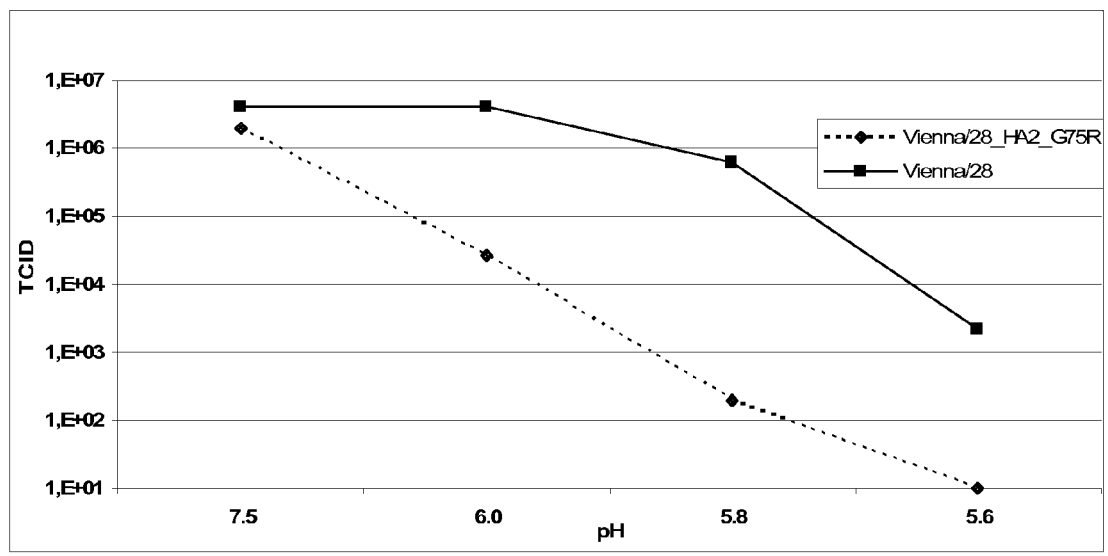

Two influenza 6:2 reassortants containing HA and NA genes from epidemic virus A/Vienna/28/06 (H3N2) and all other genes from WHO strain IVR-116 in combination with NS gene lacking the NS1 open reading frame (ΔNS1) were constructed by reverse genetics. Obtained viruses differed by one amino acid substitution in the sequence of HA2 subunit of HA molecule appeared due to different passaging conditions on Vero cells. First virus, named Vienna/28 was cultivated in the presence of medium having pH 6.5, while second virus (Vienna/28_HA2_G75R) was cultivated at standard conditions. Virus Vienna/28_ $_{HA}$2_G75R was different in the sequence of HA as compared to Vienna/28 at position G75R in the HA2 subunit which is not present in the original wild type virus. This substitution resulted in reduced infectivity of Vienna/28_HA2_G75R virus at low pH in comparison to Vienna/28 virus measured by preincubation of viruses in acidic buffers (for 30 min) with subsequent titration of infectious titer (FIG. 4).

Example 7

Virus A/Brisbane/10/2007 (egg derived, obtained from NIBSC, UK) was passaged five times on MDCK and Vero cells in parallel. After 5 passages both resulting variants were compared with the original virus for their infectivity at different values of pH in immune fluorescent assay. The obtained data clearly demonstrate that original virus A/Brisbane/10/2007 infected cells with the same efficiency at pH 5.6 and at neutral pH 7.5. But after 5 passages on corresponding cell lines both viruses lost the ability to infect cells at pH 5.6.

TABLE 3

| Viruses | Stability at pH 5.6 | Temperature of virus treatment | | | | | | |
|---|---|---|---|---|---|---|---|---|
| | | 35° C. | 40° C. | 45° C. | 50° C. | 55° C. | 60° C. | 65° C. |
| BrisbaneΔNS1 H1N1 | stable | 64 | 64 | 64 | 64 | 64 | 64 | 0 |
| WisconsinΔNS1 H3N2 | stable | 16 | 16 | 16 | 16 | 8 | 4 | 0 |
| BrisbaneΔNS1 H3N2 | stable | 16 | 16 | 16 | 16 | 8 | 4 | 0 |
| New Caledonia ΔNS1_HA2_113 | n/stable | 64 | 64 | 64 | 64 | 32 | 0 | 0 |
| WisconsinΔNS1_HA1_218_225_75_81 H3N2 | n/stable | 64 | 64 | 64 | 64 | 8 | 0 | 0 |
| HongKong156ΔNS1 H5N1 | n/stable | 32 | 32 | 32 | 16 | 0 | 0 | 0 |
| VN1203(6:2) (H5N1) | n/stable | 64 | 64 | 64 | 64 | 0 | 0 | 0 |
| VN1203 H5N1 | n/stable | 64 | 64 | 64 | 32 | 0 | 0 | 0 |
| VN1203/04 HA K58I (H5N1) | stable | 64 | 32 | 32 | 32 | 16 | 0 | 0 |

Human influenza viruses BrisbaneΔNS1 H1N1, WisconsinΔNS1 H3N2, BrisbaneΔNS1 H3N2, New Caledonia ΔNS1_HA2_113, WisconsinΔNS1_HA1_218_225_75_81 H3N2 were obtained as 6:2 reassortants bearing surface antigens HA and NA from the corresponding epidemic viruses and all other genes from IVR-116 strain. IVR-116—strain recommended by WHO for production of inactivated vaccine comprising surface glycoproteins from A/New Caledonia/20/99 (H1N1) virus. NS gene of all viruses was lacking NS1 open reading frame.

Avian viruses were obtained as 5:3 (VN1203 H5N1 and VN1203/04 HA K58I H5N1) or 6:2 (VN1203(6:2) H5N1)

Positive staining of the cells was observed only at pH 5.8 but no stained cells were visible when buffer with pH 5.6 was used (results are not shown). Sequencing of HA genes revealed that both variants acquired the same mutation at position 160 D→E in HA molecule.

Example 8

Virus A/Solomon Island/3/06 (egg derived, obtained from NIBSC, UK) was adapted to Vero cells by consecutive passages made by two different ways: at standard (neutral) conditions or at acidic (infection at pH 5.6). Resultant virus passaged at neutral pH improved the growth capacity on Vero cells from 4.7 log TCID50/ml to 6.7 log TCID50/ml, but lost the ability to infect cells at pH 5.6 in immune fluorescent assay. No stained cells were observed after infection of cells with the virus combined with buffer pH 5.6, while at neutral infection the whole monolayer was stained. Virus A/Solomon Island/3/06 adapted to growth on Vero cells using infection at acidic conditions reached the titer 7.6 log TCID50/ml and in the same time preserved the infectivity at low pH conditions. In immune fluorescent assay it was observed similar distribution of stained cells after the infection at pH 5.6 and 7.5.

Example 9

Virus A/California/7/09 of new H1N1 subtype (egg derived, obtained from CDC) was adapted to Vero cells by several consecutive passages made at acidic conditions (infection of the cells at pH 5.6). Resultant virus was named A/California/7/09-acid. Original and adapted viruses were used for the small scale (10 L) production in bioreactor with subsequent purification. The yield of A/California/7/09-acid virus measured by hemagglutination titer (HA) was higher than that of A/California/7/09 virus after each production step in 2-8 times. Results are presented in the table 4.

TABLE 4

Yield of A/California/7/09 and A/California/7/09-acid viruses

| Production step | HA titer | |
| --- | --- | --- |
|  | A/California/7/09 | A/California/7/09-acid |
| 1. Roller bottle, passage 1 | 8 | 64 |
| 2. Roller bottle, passage 2 | 16 | 64 |
| 3. Bioreactor 10 L (before harvest) | 64 | 128 |
| 4. Bioreactor 10 L (after harvest) | 8 | 64 |

Both viruses were harvested, purified according to standard procedure used for the purification of inactivated vaccines and compared. The obtained results revealed that virus A/California/7/09-acid was better than A/California/7/09 in all measured parameters (Table 5).

TABLE 5

Comparison of purified preparations of A/California/7/09 and A/California/7/09-acid viruses

| Parameters | A/California/7/09 | A/California/7/09-acid |
| --- | --- | --- |
| 1. $HA_{50\mu l}$ before/after clarification | 64/8 | 128/64 |
| 2. Titer $TCID_{50/ml}$ before/after clarification | 6.82/6.13 | 8.08/7.71 |
| 3. Yield (mg HA/L) | 1.8 | 5.4 |
| 4. HA/protein ratio | 0.58 | 0.66 |
| 5. Host cell protein impurities (Vero protein/HA) | 0.09 | 0.04 |

The invention claimed is:

1. A cell-culture adapted influenza virus produced by a method comprising the steps of:
   a) diluting influenza viruses in a solution having a pH of between 5.6 and 5.9;
   b) infecting host cells in culture with at least one infectious virus particle, wherein:
      i) the virus particle is added to said cells; and
      ii) said cells and said virus particle are incubated at a pH of between 5.6 and 5.9 to provide a virus/cell complex; c) cultivating infected host cells to propagate viruses; and
   d) harvesting the propagated viruses, wherein the virus retains infectivity at a pH range of between 5.6 and 5.8, wherein the influenza virus comprises a deletion or modification within the NS 1 gene of the virus, wherein the propagated viruses do not acquire mutations in the HA molecule when exposed to temperatures of up to 60° C. for 15 minutes, wherein hemagglutination activity of the propagated viruses is decreased less than fourfold compared with the source viruses, and wherein a titer above 7 log TCIDs0/ml is obtained from growth in cultured cells.

2. A composition useful for vaccination or therapy of viral disease comprising a cell-culture adapted influenza virus produced by a method comprising the steps of:

a) diluting source influenza viruses in a solution having a pH of between 5.6 and 5.9;
b) infecting host cells in culture with at least one infectious virus particle, wherein: i) the virus particle is added to said cells; and ii) said cells and said virus particle are incubated at a pH of between 5.6 and 5.9 to provide a virus/cell complex; c) cultivating infected host cells to propagate viruses; and d) harvesting the propagated viruses, and a pharmaceutically acceptable carrier or adjuvant, wherein the virus retains infectivity at a pH range of between 5.6 and 5.8, wherein the influenza virus comprises a deletion or modification within the NS 1 gene of the virus, wherein the propagated viruses do not acquire mutations in the HA molecule when exposed to temperatures of up to 60° C. for 15 minutes, wherein hemagglutination activity of the propagated viruses is decreased less than fourfold compared with the source viruses, and wherein a titer above 7 log TCIDs0/ml is obtained from growth in cultured cells.

3. The influenza virus of claim 1, wherein the host cells used to propagate the virus are selected from the group consisting of BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, TCMK cells, LLC-PK cells, PK15 cells, W1-38 cells, MRC-5 cells, BHK cells, SP2/0 cells, NS0 cells, and PerC6 cells.

4. The composition of claim 2, wherein the host cells used to propagate the viruses are selected from the group consisting of BSC-1 cells, LLC-MK cells, CV-1 cells, CHO cells, COS cells, murine cells, human cells, HeLa cells, 293 cells, VERO cells, MDBK cells, MDCK cells, MDOK cells, CRFK cells, TCMK cells, LLC-PK cells, PK15 cells, W1-38 cells, MRC-5 cells, BHK cells, SP2/0 cells, NS0 cells, and PerC6 cells.

* * * * *

SEQUENCE LISTING

```
<160> NUMBER OF SEQ ID NOS: 2

<210> SEQ ID NO 1
<211> LENGTH: 15
<212> TYPE: DNA
<213> ORGANISM: Influenza A virus

<400> SEQUENCE: 1
attgacaaaa tgaac                                                   15

<210> SEQ ID NO 2
<211> LENGTH: 15
<212> TYPE: DNA
<213> ORGANISM: Influenza A virus

<400> SEQUENCE: 2
attgacatta tgaac                                                   15
```